United States Patent
Kondo et al.

[11] Patent Number: 5,873,866
[45] Date of Patent: Feb. 23, 1999

[54] FLEXIBLE SHEATHING TUBE CONSTRUCTION, AND METHOD FOR FABRICATION THEREOF

[75] Inventors: Mituo Kondo; Hirokazu Kobayashi; Nobuharu Takahashi, all of Omiya, Japan

[73] Assignee: Fuji Photo Optical Co., Ltd., Omiya, Japan

[21] Appl. No.: 881,159

[22] Filed: Jun. 24, 1997

Related U.S. Application Data

[63] Continuation of Ser. No. 583,162, Jan. 4, 1996.

[30] Foreign Application Priority Data

Jan. 13, 1995 [JP] Japan .................................. 7-019891
May 30, 1995 [JP] Japan .................................. 7-154103
May 18, 1995 [JP] Japan .................................. 7-142397

[51] Int. Cl.$^6$ .................................................. A61M 25/00
[52] U.S. Cl. ....................... 604/280; 604/264; 600/140; 600/143
[58] Field of Search .................... 604/264, 280–2; 600/139–141, 143

[56] References Cited

U.S. PATENT DOCUMENTS

| | | | |
|---|---|---|---|
| 4,753,222 | 6/1988 | Morishita | 600/140 |
| 4,805,595 | 2/1989 | Kanbara | 600/140 |
| 4,899,787 | 2/1990 | Ouchi et al. | 604/282 |
| 5,002,041 | 3/1991 | Chikama | 600/139 |
| 5,137,013 | 8/1992 | Chiba et al. | 604/282 |
| 5,275,152 | 1/1994 | Krauter et al. | 600/140 |
| 5,279,596 | 1/1994 | Castaneda et al. | 604/280 |
| 5,423,848 | 6/1995 | Washizuka et al. | 604/264 |
| 5,465,710 | 11/1995 | Miyagi et al. | 604/282 |
| 5,482,029 | 1/1996 | Sekiguchi et al. | 604/280 |
| 5,484,424 | 1/1996 | Cottenceau et al. | 604/282 |
| 5,522,875 | 6/1996 | Gates et al. | 604/282 |
| 5,531,721 | 7/1996 | Pepin et al. | 604/282 |
| 5,538,513 | 7/1996 | Okajima | 604/282 |

*Primary Examiner*—Wynn Wood Coggins
*Assistant Examiner*—Jennifer R. Sadula
*Attorney, Agent, or Firm*—Oblon, Spivak, McClelland, Maier & Neustadt, P.C.

[57] ABSTRACT

A flexible sheathing tube suitable for encasing an elongated flexible body like a flexible insertion rod of an endoscope or other insertion type examination istrument, and a method for fabrication of such sheathing tubes. The flexible sheathing tube being of the type is basically provided with a flexible base structure having at least an open helical coil member of a cylindrical shape, a protective mesh sleeve fitted on the helical coil member, and an insulating outer coating layer formed on the protective mesh sleeve. The sheathing tube is further provided with an inner coat layer of a resilient material formed on the inner side of the helical coil member in such a manner as to cover the inner periphery of the helical coil member completely, filling in gap spaces between open helices of the coil member.

13 Claims, 8 Drawing Sheets

F I G. 3
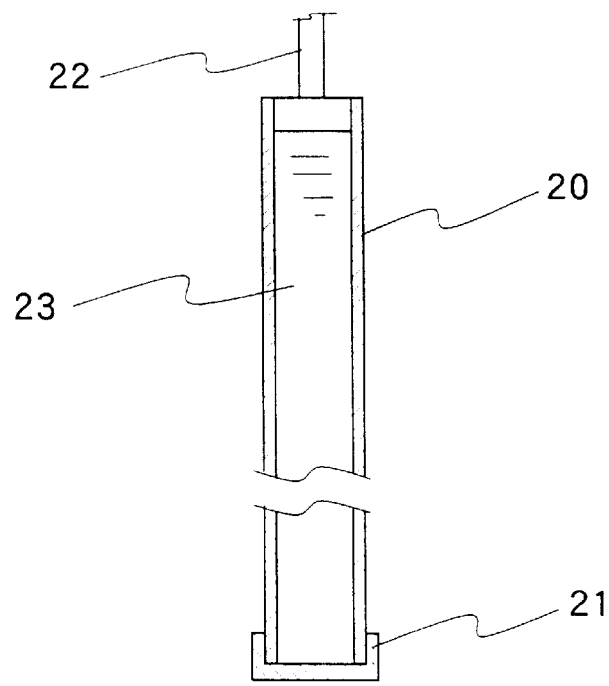
F I G. 4
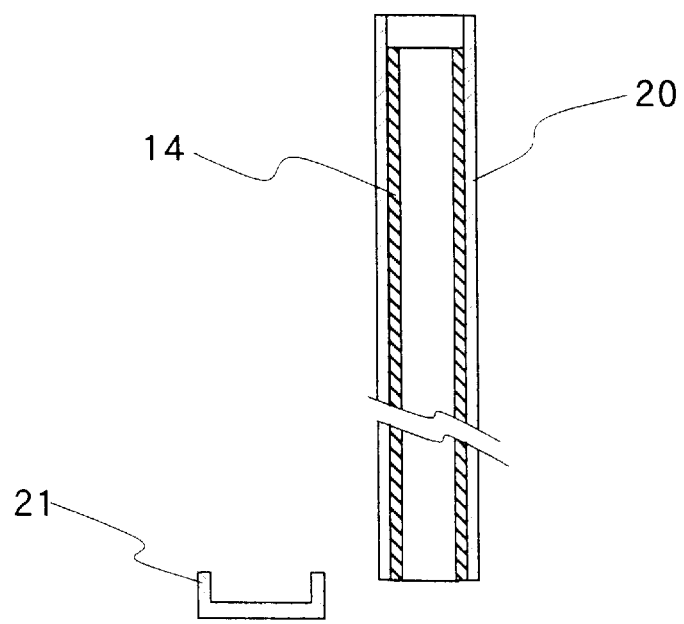

FLEXIBLE SHEATHING TUBE CONSTRUCTION, AND METHOD FOR FABRICATION THEREOF

This application is a continuation of application Ser. No. 08/583,162, filed on Jan. 4, 1996, now abandoned.

BACKGROUND OF THE INVENTION

1. Field of the Art

This invention relates to a flexible sheathing tube construction particularly suitable for use on insertion type examination instruments having a flexible elongated component part fitted in a flexible sheathing tube as in the case of flexible insertion rods of endoscopes and ultrasound probes which are designed to be introduced into internal cavities in humane bodies or machines or other internal spaces, and a method for fabrication of such flexible sheathing tube.

2. Prior Art

For instance, an endoscope, which is typical of instruments designed to be introduced into internal cavities or spaces in human bodies or machines for examination purposes, is largely constituted by a manipulating head assembly providing manipulating control means for the endoscope, an elongated flexible insertion rod containing a component part or parts for carrying out examinations in intracavitary portions of human body and extended forwardly from the manipulating head assembly, and a flexible universal cable extended rearward from the manipulating head assembly to connect the endoscope detachably to an illumination light source or to a signal processing unit in case of an electronic endoscope. Except for a proximal end portion which is connected to the manipulating head assembly and a short rigid tip end section which accommodates endoscopic observation means at the distal end of the endoscope, the endoscopic insertion rod is constituted by a tubular flexible rod section almost over its entire length, the flexible rod section being capable of flexibly bending its body into conformity with the shape of a path of insertion. Normally, the flexible rod section is connected to the rigid tip end section through an angle section which can be manipulated through an angle knob provided on the manipulating head assembly to turn the rigid tip end section into a desired direction.

In order to illuminate dark intracavitary portions under endoscopic observation, the rigid tip end section is normally provided with an illumination window in addition to an observation window, permitting the operator to observe intracavitary regions of particular interest under illuminated conditions. Accordingly, it is essential for an endoscopic observation means to have an illumination system in combination with an endoscopic observation system.

Typically, an endoscopic illumination system is constituted by a light guide in the form of a bundle of extra fine fiber optics, and an illumination window located in front of a light emitting end of the light guide to disperse illumination light rays over a predetermined range within an intracavitary region. The light guide is extended through the entire length of the insertion rod and down to the proximal end of the universal cable via the manipulating head assembly.

On the other hand, an endoscopic observation system includes an objective lens which is fitted in the observation window, and an image pickup means which is located at the focus of the objective lens, i.e., an electronic image sensor like a CCD or a light entrance end of an optical image guide in the form of a fiber optics bundle or the like. In case of an electronic endoscope, a signal cable from a CCD is also passed through the flexible insertion rod and the universal cable via the manipulating head assembly together with the afore-mentioned illumination light guide. In case of an optical endoscope, an image guide is passed through the flexible insertion rod up to an eyepiece which is connected to the housing of the manipulating head assembly of the endoscope.

In addition to the above-described endoscopic illumination and observation systems which are minimum essentials, endoscopes are generally provided with means for bioptic or therapeutic treatments such as sampling of cells, extraction of diseased portions, stanching etc. In order to permit insertion of forceps, high frequency surgical instruments or other instruments which are necessary for these treatments, endoscopes are provided with the so-called biopsy channel extending from the manipulating head assembly down to the distal end of the flexible insertion rod. Besides, it is often the case that the endoscopic insertion rod includes a cleansing means for cleaning the observation window which is susceptible to contaminations with body fluids. An observation window cleansing means of this sort usually includes an air/water feed nozzle which is located and opened in the proximity of the observation window at the distal end of the insertion rod. The air/water feed nozzle is connected to an air/water feed tube which is placed in the rigid tip end section and the angle section of the endoscopic insertion rod. In the flexible rod section, the air/water tube is bifurcated into an air feed tube and a water feed tube which are extended all through the flexible rod section up to air and water supply ports on the manipulating head assembly of the endoscope.

Accordingly, the flexible rod section of the endoscopic insertion rod needs to receive therein the abovedescribed light guide, signal cable (or image guide) which are extended to or from the endoscopic observation means on the rigid tip end section, and in some cases need to further receive the biopsy channel, air feed tube and water feed tube as mentioned above. As explained hereinbefore, the flexible rod section should be capable of bending its body in arbitrary directions in conformity with the shapes of various bends in a path of insertion. Therefore, the light guide or other elongated members to be fitted in the flexible rod section need to be formed of a flexible or pliable material.

Further, the flexible rod section which contains fragile component part like a light guide is required to have satisfactory properties in shape retainability and anti-crushing strength, together with unresisting bending flexibility for advancement along a path of insertion which could take various shapes. In other words, despite the requirement for easily bending pliability, the flexible rod section is at the same time required to have a structure which is rigid enough for transmitting a propelling thrust securely to the rigid tip end section at the time of insertion into an intracorporeal portion to be examined.

In order to satisfy these requirements, the flexible rod section of an endoscope is usually composed of a flexible tubular base structure in the form of an open helical coil structure which is formed by winding a narrow thin resilient metal strip helically into a cylindrical shape in a predetermined open pitch, a protective mesh sleeve of wire netting which is fitted on the helical substructure, and an outer skin layer of a resilient synthetic resin material laminated to cover the protective net. Usually, the flexible base structure of the sheathing tube has a double coil construction consisting of inner and outer open helical coil members of opposite winding directions. The protective mesh sleeve is impregnated with an adhesive and thereby securely bonded to the respective open helical coil members of the flexible base structure. The flexible sheathing tube, which is composed of, from the inner side, a flexible base structure of the double coil construction, a protective mesh sleeve and an outer skin layer in the above-described manner, can perform the functions of flexibly bending an insertion rod in desired directions and retaining the shape of the rod, particularly, the shape of the internal space of the insertion rod against deformations.

However, in addition to the above-described requirements, the flexible sheathing tube of the endoscopic insertion rod has to meet other requirements, for example, smooth operationability at the time of insertion into the body of a patient and reductions in diameter for lessening pains on the part of patient. In this regard, if one tries to reduce the diameter of the flexible sheathing tube while maintaining its shape retainability and anti-crushing strength, there will arises a problem of frictional contact of internally fitted endoscopic component parts such as the light guide and biopsy channel, with each other or with inner surfaces of the flexible sheathing tube itself. Accordingly, it becomes necessary to provide measures for protecting these internally fitted components against damages which might result from such frictional contact, particularly, from frictional contact with the helical metal coil members on the innermost position of the flexible sheathing tube. This is because, even if the metal strips of the open helical coil members were rounded off beforehand at the respective lateral side edges, they would still have possibilities of damaging or breaking a fragile component part like the light guide easily when forced into frictional sliding contact with each other. Besides, considering the use of a high frequency surgical instrument through the biopsy channel, preferably any metal member should not be allowed to remain in an exposed state on the inner side of the flexible sheathing tube.

Further, since the inner and outer metal coil members of the above-mentioned flexible base structure of the sheathing tube are in the form of open helical coils each having the respective helices spaced from each other by a gap space of a predetermined width and placed in position in an overlapped state in surface contact with helices of other coil member, it is very likely for the inner and outer helical coil members to be subjected to a twisting force in different degrees and in different directions when a bending force is exerted on the insertion rod, resulting in relative sliding contact of the two helical coil members and in irregular spacings between the individual helices of the respective coil members. As soon as the insertion rod is stretched again into a rectilinear form, normally such irregularly spaced helices restore original regularly spaced conditions by resiliency of the coils. However, if the flexible insertion rod section is bent repeatedly to exert deformative forces on the flexible sheathing tube at a relatively high frequency, the individual helices of the inner and outer coil members tend to remain in irregularly spaced positions, giving rise to irregularities in rigidity in the axial direction of the endoscopic insertion rod.

From a standpoint of higher adaptability of the insertion rod to a path of insertion, the sheathing tube is preferred to have as high flexibility as possible. However, the higher the flexibility of the sheathing tube, the lower becomes the strength in stretching and contracting directions of the insertion rod. Accordingly, at the time of insertion of the flexible insertion rod, there might occur a situation in which a fore end portion of the flexible sheathing tube is compressed too easily, narrowing the spacings between the helices in that portion to such a degree as to lower the flexibility of the insertion rod conspicuously in bending directions. Besides, application of a compressive force on the flexible sheathing tube could cause detachment of the protective mesh sleeve off the outer helical coil member, which in turn could lead to a detrimental damage to the outer skin layer of the sheathing tube. Namely, a flexible sheathing tube which has an outer and inner helical coil members simply superposed one on the other cannot be considered to be sufficient in durability and reliability.

Particularly, an axial fore end portion of the endoscopic insertion rod is required to have a high degree of flexibility to ensure its easy bending motions along a path of insertion. On the other hand, on the side of the proximal end, the insertion rod is required to have a certain degree of rigidity to improve transmission of a propelling force or thrust through the rod being advanced toward an intracavitary portion of interest. As for means for controlling the rigidity in the axial direction of the flexible sheathing tube, attempts have been made to vary the width of metal strips for the helical coil members or of gap spaces between the respective helices of the coil members which are wound in an open pitch, to vary the mesh size of the protective mesh sleeve, or to vary the amount of application of an adhesive in the axial direction of the sheathing tube. Since all of these means have inherent problems, there have been strong demands for improved means which can vary the rigidity in the axial direction of the flexible sheathing tube in a stable and reliable manner.

SUMMARY OF THE INVENTION

With the foregoing situations in view, it is an object; of the present invention to provide a flexible sheathing tube construction suitable for encasing an elongated flexible body securely in a protected state, and particularly suitable for use on a flexible insertion rod of an endoscope or other insertion type examination instruments, the flexible sheathing tube having controlled flexibility in the axial direction thereof to ensure improved controllability and maneuverability of an insertion rod or the like at the time of introduction into an internal cavity to be examined.

It is another object of the present invention to provide a flexible sheathing tube of the sort as mentioned above, which is suitable for sheathing an elongated fragile component part such as endoscopic light guide or the like securely in a protected state.

It is still another object of the invention to provide a flexible sheathing tube particularly suitable for use on an endoscopic flexible insertion rod containing a biopsy channel for insertion of a high frequency surgical instrument or the like, the flexible sheathing tube being interiorly provided with an electrical insulation keeping metallic helical coil members of a flexible base structure of the sheathing tube securely out of electrical contact with such a high frequency instrument.

It is a further object of the present invention to provide a flexible sheathing tube for an endoscopic insertion rod, which is arranged to suppress frictional sliding contact of inner and outer open helical coil members of a flexible base structure of the sheathing tube even in the event a compressive force is applied on the sheathing tube, thereby preventing open helices of the respective coil members from being spaced irregularly to such a degree as to cause conspicuous irregular variations in rigidity in the axial direction of the endoscopic insertion rod.

It is another object of the invention to provide a flexible sheathing tube which can prevent detachment of a protective mesh sleeve from a helical coil member of a flexible base structure of the sheathing tube, precluding damages as would be caused to an outer skin layer by detachment of the protective mesh sleeve.

It is still another object of the invention to provide a flexible sheathing tube of the sort as mentioned above, which is capable of maintaining predetermined variations in rigidity in a stabilized state in the axial direction of the tube.

In accordance with the present invention, the above-stated various objectives are achieved by the provision of a flexible sheathing tube of the sort composed of, from the inner side, a flexible base structure consisting of at least an open helical coil member wound in a cylindrical shape in a predetermined open pitch, a protective mesh sleeve fitted on the helical coil member, and an insulating coating layer formed on the protective mesh sleeve, characterized in that the flexible sheathing tube is provided with an inner coat layer of a resilient material formed on the inner side of the helical coil member in such a manner as to cover the inner periphery of the helical coil member completely, filling in gap spaces between individual helices of the coil member. In this flexible sheathing tube construction, the flexible base structure may further include, in overlapping relation with the first open helical coil member with open helices, a second open helical coil member with open helices of the opposite winding direction relative to the helices of the first helical coil member, and an intermediate mesh sleeve fitted between the first and second coil members.

In accordance with the present invention, there is also provided a method for fabricating a flexible sheathing tube of the construction as defined above, the method essentially including the steps of: fitting a protective mesh sleeve on an open helical coil before or after forming an insulating outer coat layer thereon; pouring a liquidized resilient material into the helical coil through one end thereof while closing the other end with a closure means; holding the liquidized resilient material in the helical coil over a predetermined time length; removing the closure means to let the liquidized resilient material drain out of the helical coil, leaving a deposition layer of the resilient material on the inner periphery and between the helices of the open helical coil; and drying the deposition layer of the resilient material.

Further, in order to vary rigidity in the axial direction of the flexible sheathing tube by way of the resilient inner coat layer, the fabrication method may comprise the steps of: pouring a first liquidized resilient material into the open helical coil through one end thereof while closing the other end with a closure means as described above; holding the first liquidized resilient material in the helical coil for a predetermined time length; putting the closure means on and off the other end of the coil member for a number of times to form a first deposition layer of the resilient material on the inner periphery and between open helices of the helical coil; pouring a second liquidized resilient material of different property or density from the first liquidized resilient material into the helical coil through the opposite end thereof up to a parting line of the first deposition layer while stopping the other end with a closure means; holding the second liquidized resilient material in the helical coil for a predetermined time length; and removing the closure means to let the second liquidized resilient material drain out of the helical coil, leaving a second deposition layer of different flexibility on the inner periphery and between open helices of the helical coil.

BRIEF DESCRIPTION OF THE DRAWINGS

The above and other objects, features and advantages of the invention will become apparent from the following particular description of the invention, taken in conjunction with the accompanying drawings which show by way of example some preferred embodiments of the invention and in which:

FIG. 3 is a schematic illustration of a stage of forming a resilient coat layer on the inner periphery of a flexible base structure of the sheathing tube of the first embodiment;

FIG. 4 is a schematic illustration of another stage of forming a resilient coat layer on the inner periphery of the flexible base structure of the sheathing tube;

DESCRIPTION OF PREFERRED EMBODIMENTS

Figure 1:
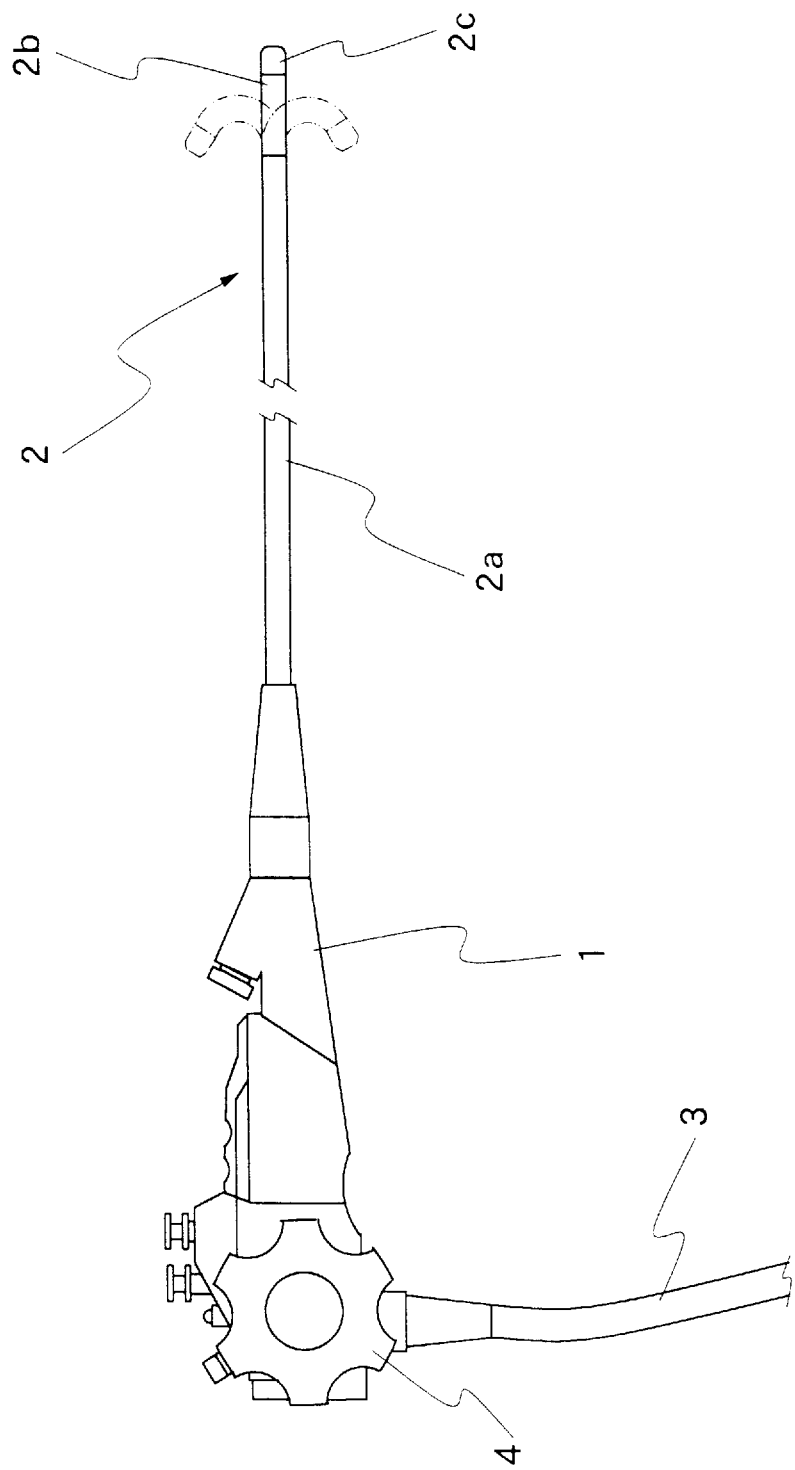
FIG. 1 is a schematic view of a typical endoscope, showing the layout of its major parts.

Referring first to FIG. 1, there is shown a layout of major components of an endoscope, which is typical of insertion type examination instruments. In this figure, indicated at 1 is a manipulating head assembly of the endoscope, at 2 is a flexible insertion rod to be introduced into an intracavitary portion which needs endoscopic examination or observation, and at 3 is a flexible universal cable which connects the endoscope to a light source and/or an electrical or ultrasound signal processor depending upon the type of the endoscope concerned. In case the endoscope is of the sort which is arranged for medical use, a flexible rod section 2a extends almost over the entire length of the insertion rod 2 from its proximal end which is connected to the manipulating head assembly 1 to its fore end which is successively connected to an angle section 2b and a rigid tip end section 2c. The flexible rod section 2a needs to be capable of bending its body in arbitrary directions in conformity with the shape of a path of insertion. Opened in the distal end face of the rigid tip end section 2c are an illumination window and an observation window of endoscopic observation means, along with an exit opening of a biopsy channel for insertion of forceps or other bioptic or surgical instruments. The angle section 2b can be bent in an arbitrary direction through manipulation of an angle knob 4 on the manipulating head assembly 1 to turn the rigid tip end section 2c in a desired direction.

The endoscopic flexible insertion rod 2, which is designed to be inserted into dark intracavitary portions of patient, should be able to project illumination light through the illumination window toward an intracavitary region under observation through the observation window. For this purpose, a flexible light guide is passed through the universal cable 3 and the insertion rod 2 to the rigid tip end section 2c via the manipulating head assembly 1. At the proximal end of the universal cable 3, the light guide is disconnectibly connected to a light source. Illumination light from the light source is transmitted through the light guide to its fore light emitting end which is disposed face to face with the illumination window on the distal end face of the rigid tip end section 2c. Further, in case of an electronic endoscope which employs an electronic image pickup means like CCD as endoscopic observation means, a signal cable from an image pickup means which is located face to face with the observation window is also passed through the flexible rod section 2a and the universal cable 3 along with the light guide via the manipulating head assembly 1. At the proximal end of the universal cable 3, the signal cable from the electronic image pickup means is connected to a connector member, which is in turn disconnectibly connected to a video signal processor.

Figure 2:
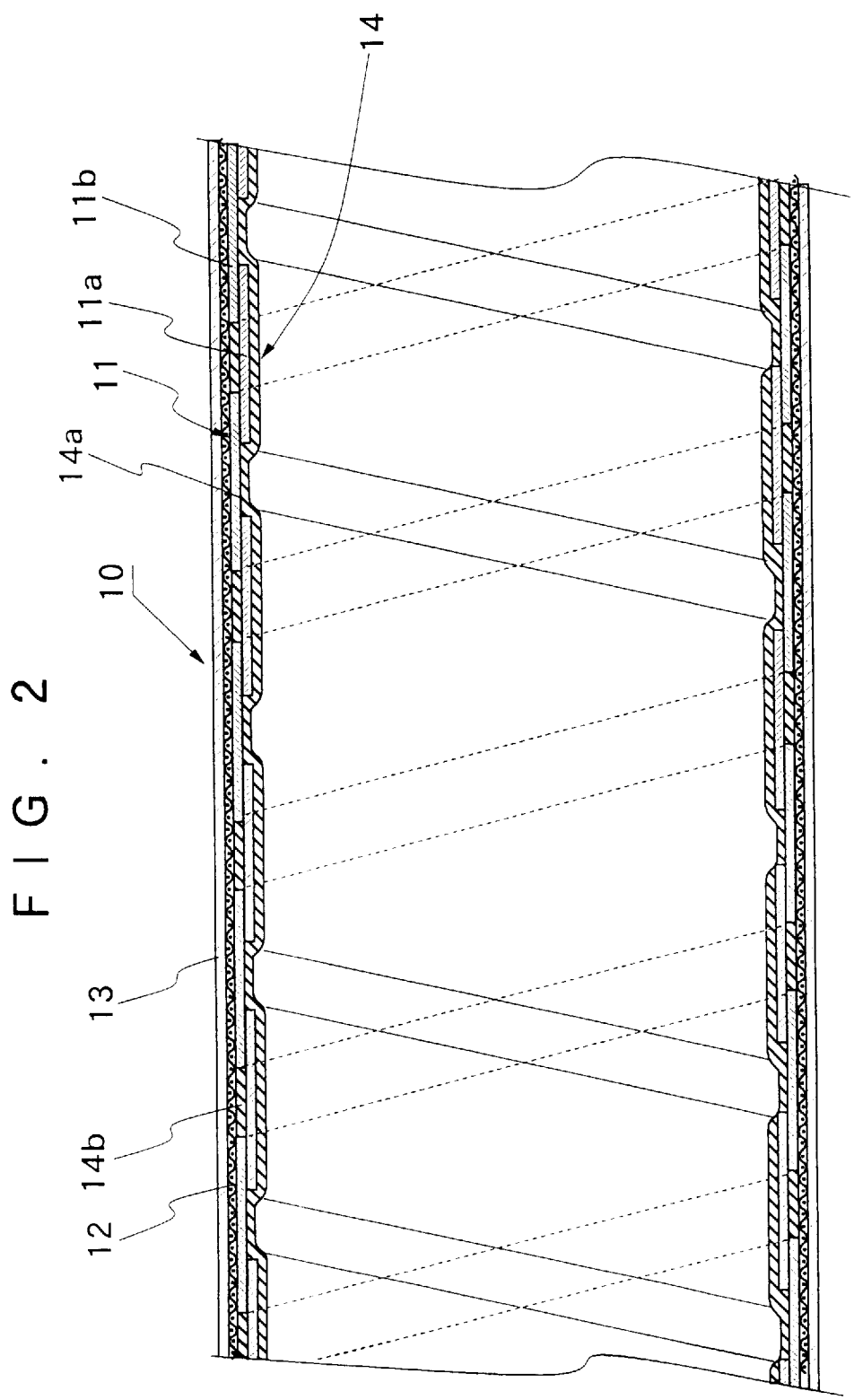
FIG. 2 is an enlarged fragmentary sectional view of a flexible sheathing tube in a first embodiment of the present invention.

As mentioned hereinbefore, the flexible rod section 2a of the endoscopic insertion rod 2 is required to be able to bend its body in arbitrary directions in conformity with the shape of a path of insertion, and therefore the above-described light guide, biopsy channel and signal cable are all fitted in a flexible sheathing tube 10 of the construction as shown particularly in FIG. 2. In FIG. 2 and following figures, the component parts which are fitted in the flexible sheathing tube 10 are omitted for the sake of simplicity of illustration.

As seen in FIG. 2, located in the innermost position of the flexible sheathing tube 10 is a flexible base structure in the form of an open helical coil member 11 which is formed by helically winding a narrow metal strip in a predetermined open pitch. In this particular embodiment, the flexible base structure of the sheathing tube 10 consists of a couple of open helical coil members which are fitted one on the other in an overlapped state, namely, an inner open helical coil member 11a and an outer open helical coil member 11b having open helices of opposite winding directions. A mesh sleeve 12 of fine metal wire netting is fitted on the double coil base structure 11, i.e., on the open helical coils 11a and 11b, to form a protective mesh layer therearound. The protective mesh sleeve 12 is impregnated with an adhesive and thereby securely bonded to the open helical coil members 11. Laminated on the protective mesh sleeve 12 is an outer skin layer 13 of a resilient material such as urethane resin or the like.

Indicated at 14 is an inner coat layer of an electrically insulating resilient material such as natural rubber, urethane rubber or the like. This inner coat layer 14 is formed in such a way as to cover completely the inner periphery of the inner coil member 11a of the double coil structure 11, more specifically, to cover the inner side of the inner coil member 11a and at the same time fill in gap spaces between the individual helices of the inner and outer open coil members 11a and 11b by way of filler portions 14a and 14b. Accordingly, the individual helices of the inner and outer open coil members 11a and 11b are more or less embedded in the resident material of the inner coat layer 14 which fills the gap spaces between the respective helices.

In this instance, the inner coat layer 14 can be formed over the entire length of the flexible sheathing tube 10 either uniformly in terms of its thickness and resiliency or with a predetermined gradation or variations in flexibility or rigidity in the axial direction, for example, to provide an endoscopic insertion rod which has higher rigidity at its proximal end than in its fore end portion which is connected to the angle section 2b of the flexible insertion rod 2. In this regard, the degree of flexibility or rigidity of the inner coat layer can be varied by changing its properties or thickness axially along the elongated body of the flexible sheathing tube, for example, in order to impart a higher degree of flexibility to a fore end portion of an endoscopic insertion rod to be inserted into intracavitary regions of patient while imparting a higher degree of rigidity to a rear end portion which is always located outside during endoscopic examination.

The above-described inner coat layer 14 can be formed by a method as illustrated in FIGS. 3 and 4.

In the first place, the protective mesh sleeve 12 is fitted on the flexible double coil structure 11, and an adhesive agent is impregnated into the protective mesh sleeve 12 for secure bondage to the double coil structure 11. An outer skin layer 13 is then laminated on the protective mesh sleeve 12 to form a sheathing tube pre-assembly 20 for the flexible sheathing tube 10 as shown in FIG. 3. Thereafter, a closure means 21 is fitted on one end of the sheathing tube pre-assembly 20, namely, at one end which will form a proximal end of an endoscopic insertion rod in case the sheathing tube is to be applied to an endoscope. More specifically, the closure means 21 is tightly and securely fitted on one end of the sheathing tube pre-assembly 20. A rubber solution 23 prepared by dissolving rubber in a solvent, is then filled in the sheathing tube pre-assembly 20 via feed pipe 22 to deposit an inner coat layer 14 interiorly of the pre-assembly 20.

While the rubber solution is retained within the sheathing tube pre-assembly 20 for a predetermined time length, rubber deposits on the inner surfaces of the inner helical coil member 11a of the flexible coil structure 11 and at the same time fills in the gap spaces between the individual helices of the inner and outer helical coil members; 11a and 11b. When the closure means 21 at one end of the sheathing tube pre-assembly 20 is removed as shown in FIG. 4, excess rubber solution is discharged therethrough, leaving a deposition rubber layer of a predetermined thickness on the inner periphery of the flexible sheathing tube pre-assembly 20. Upon drying out the deposition rubber layer, it cures into a form which can serve as the above-described inner coat layer 14. While the deposited rubber layer is being dried, the rubber deposit which is still in a liquidized state tends to flow gradually in the downward direction. Therefore, by slowing down the drying speed, the thickness of the inner coat layer 14 can be varied gradually in the axial direction from the top upper to bottom end of the sheathing tube 10.

Figure 5:
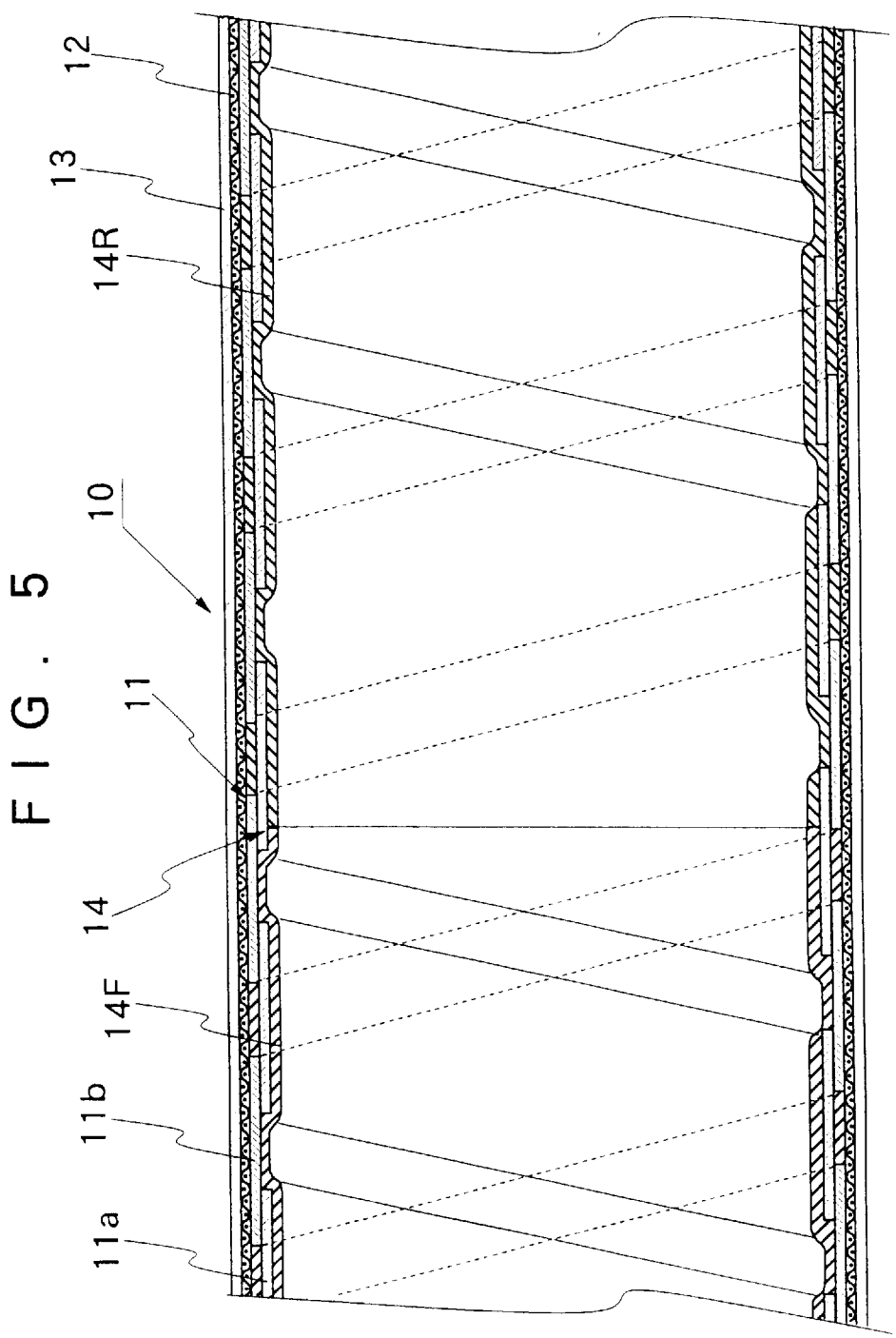
FIG. 5 is a view similar to FIG. 2 but showing a flexible sheathing tube according to a second embodiment of the invention.
Figure 6:
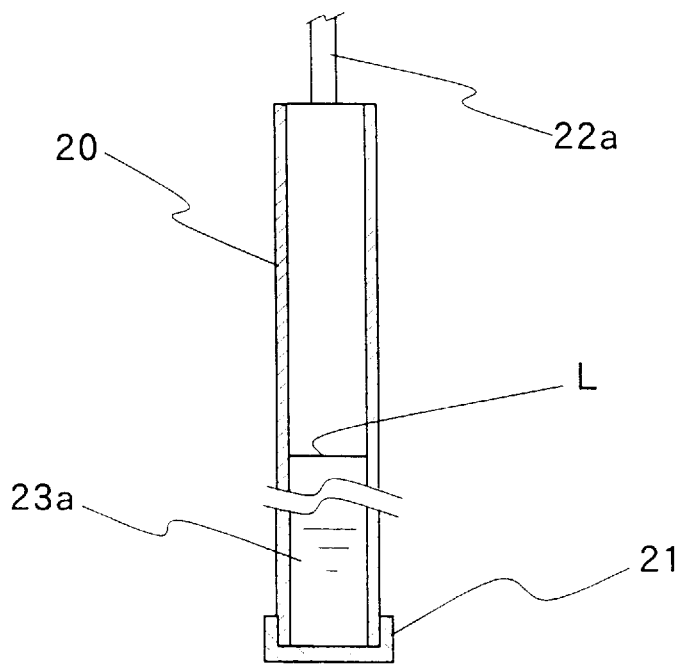
FIG. 6 is a schematic illustration of a stage of forming a resilient coat layer on the inner periphery of a flexible base structure of the sheathing tube of the second embodiment.
Figure 7:
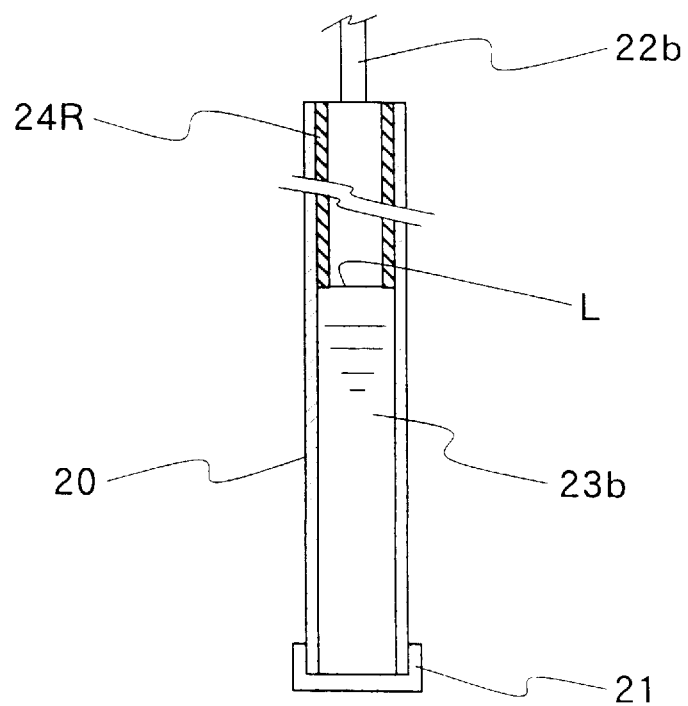
FIG. 7 is a schematic illustration of another stage of forming a resilient coat layer on the inner periphery of the flexible base structure of the sheathing tube of the second embodiment.

Shown in FIG. 5 is a flexible sheathing tube construction with an inner coat layer which has different characteristics or properties on front and rear parts of the sheathing tube 10. In this case, the flexibility of the inner coat layer is varied by forming a first inner coat layer 14R of low flexibility in a rear part of the sheathing tube pre-assembly 20 and a second inner coat layer 14F of higher flexibility in a front part. FIGS. 6 and 7 show a method for forming such an inner coat layer with different properties in flexibility at the opposite ends thereof. Firstly, as shown in FIG. 6, a first rubber solution 23a which, is supplied through a first feed pipe 22a, is poured into a sheathing tube pre-assembly 20 which is closed at its lower end by a closure means 21, filling the first rubber solution 23a up to a predetermined level L in the axial direction of the sheathing tube pre-assembly 20. Upon lapse of a predetermined time length, the closure means 21 is removed from the lower end of the assembly 20 to drain excess rubber solution 23a therethrough, followed by drying of a deposition rubber layer which remains in the sheathing tube pre-assembly 20, to form one inner coat layer (e.g., the first inner coat layer 14R) on part of the inner periphery of the sheathing tube assembly 20. Thereafter, the sheathing tube pre-assembly 20 is turned upside down, and the closure means 21 is fitted on the other end of the assembly 20 which is now on the lower side. In a next stage, as shown in FIG. 7, a second rubber solution 23b, which is supplied through a feed pipe 22b, is filled in the sheathing tube pre-assembly 20 until the second rubber solution 23b reaches a level of a parting line or a border line of the first inner coat layer 24R formed by the first rubber solution 23a. After holding the second rubber solution 23b in the sheathing tube pre-assembly 20 over a predetermined time length, the closure means 21 is removed from the lower end of the sheathing tube pre-assembly 20 to drain excess second rubber solution therethrough. A deposition rubber layer which remains in the sheathing tube pre-assembly 20 is then dried to form another inner coat layer of different properties (e.g., the second inner coat layer 14F) on the inner periphery of the sheathing tube pre-assembly 20 on the other side of the above-mentioned parting line. In case the flexible sheathing tube 10 is to be ultimately assembled into an endoscopic insertion rod, it is preferred to employ a quick-drying type rubber solution especially for the second inner coat layer 14F which is to be located on the front side of the insertion rod where it is undesirable for the rubber deposition layer to pick up thickness while drying, as compared with the first inner coat layer 14R to be located on the rear side of the insertion rod.

In case the flexible sheathing tube 10 of the above-described construction is fitted on a flexible rod section 2a of an endoscopic insertion rod 2, the insertion rod 2 is met by resisting forces upon introduction into the body of patient. Particularly in case of an endoscope which is designed for examination of large intestine, the introduction of the insertion rod 2 is resisted by extremely large forces. Therefore, in order to push in the insertion rod 2 straight forward, it becomes necessary to transmit a thrust or a propelling force effectively all the way to the fore tip end of the rod. On such an occasion, despite the resiliency in physical properties, the resilient rubber material of the inner coat layer 14 which, by way of the afore-mentioned filler portions 14a and 14b, completely fills in the gap spaces between the respective open pitch helices of the inner and outer coil members 11a and 11b of the flexible base structure 11 which extends through the entire length of the flexible rod section 2a, functions to transmit a thrust or a propelling force securely to the rigid tip end section 2c at the distal end of the insertion rod 2. Accordingly, at the time of insertion into an intracavitary portion, there are less possibilities of the insertion rod 2 being forcibly bent by a resistive force in its rear end portion outside the body of patient to such a degree as to make a further advancement of the rod impossible.

Of course, the filler portions 14a and 14b which fill in the gap spaces between the individual helices of the inner and outer coil members 11a and 11b are resilient enough for permitting smooth flexing movements of the insertion rod 2 along a path of insertion. A propelling thrust can be transmitted more efficiently to the rigid tip end section 2c of the insertion rod 2 especially in case the inner coat layer 14 of the sheathing tube 10 consists of two sections of different properties in flexibility, i.e., a first inner coat layer 14R of lower flexibility formed on the rear side and a second inner coat layer 14F of higher flexibility formed on the front side of the flexible sheathing tube 10, for imparting higher flexibility to a fore end portion of the insertion rod which has to be bent in arbitrary directions along a path of insertion, while imparting higher rigidity to a rear end portion of the insertion rod which is normally located outside the body of patient to transmit axial propelling forces toward the fore end of the insertion rod. When the insertion rod is bent, the filler portions 14a and 14b of resilient material in a bent rod portion undergo elastic deformations, but they restore initial conditions as soon as the insertion rod is straightened again, maintaining gap spaces of a predetermined width between the respective helices of the inner and outer coil members 11a and 11b. Therefore, there are less possibilities of irregular variations in rigidity developing in a particular region of the flexible rod section 2a during use over an extended period of time.

When the insertion rod 2 is bent in conformity with the shape of a path of insertion as mentioned hereinbefore, the elongated component parts which are fitted in the insertion rod 2, including the light guide, biopsy channel and so forth, are caused to move in radially outward and inward directions as well as in axial directions in relation with flexures of the insertion rod. On such occasions, however, the internally fitted component parts are caused to slide along the inner surface of the flexible sheathing tube 10, namely, in contact with the surfaces of the resilient inner coat layer 14 which covers and holds the flexible coil structure 11 in an unexposed state to preclude possibilities of damages to the internally fitted component parts.

The rubber material which constitutes the inner coat layer 14 is not necessarily of lubricative or anti-frictional nature by itself. That is to say, for the purpose of lessening frictions between the inner coat layer 14 and internally fitted components of the insertion rod, the inner coat layer 14 may contain powdery anti-friction material such as molybdenum disulfide, carbon or the like. Such powdery anti-friction material can be mixed into the rubber solution before forming the inner coat layer 14, or applied on wet surfaces of the inner coat layer 14 before drying. Alternatively, powdery anti-friction material may be filled in the flexible sheathing tube after formation of the inner coat layer 14 so that it deposits on the surfaces of the internally fitted component parts and the inner coat layer 14 to be brought into sliding contact with each other. The inner coat layer 14 which is formed of a resilient material can be easily treated by any one of these methods to bear powdery anti-friction material securely on its surfaces. Besides, once deposited, the powdery anti-friction material tends to sink into the surfaces of the resilient inner coat layer 14 without being shifted into particular localities by sliding movements of the internally fitted component parts, thus ensuring their smooth sliding movements at any point within the length of the flexible sheathing tube 10.

Further, the metallic component parts of the flexible sheathing tube 10, that is, the flexible coil structure 11 and the protective wire mesh sleeve 12 are sandwiched securely in an electrically insulated state between the outer skin layer 13 and the inner coat layer 14. Therefore, even if a high frequency surgical instrument is inserted through the biopsy channel, there are no possibilities of electrical conduction taking place through the metallic parts of the sheathing tube or to the manipulating head assembly 1 of the endoscope, which might lead to accidents due to electric shocks to the operator who grips a manipulating control means on the head assembly 1.

Figure 8:
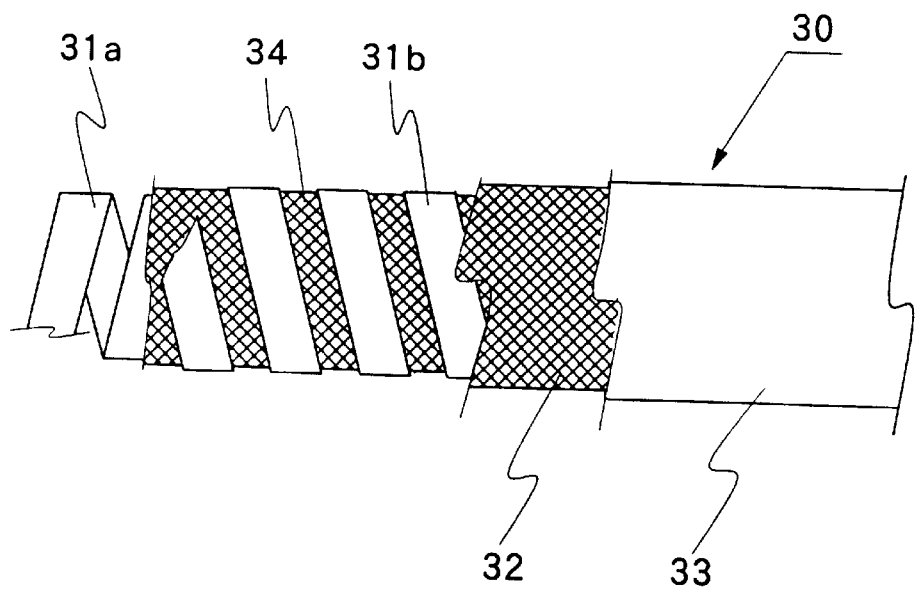
FIG. 8 is a schematic partly removed view of a flexible sheathing tube in a third embodiment of the invention.
Figure 9:
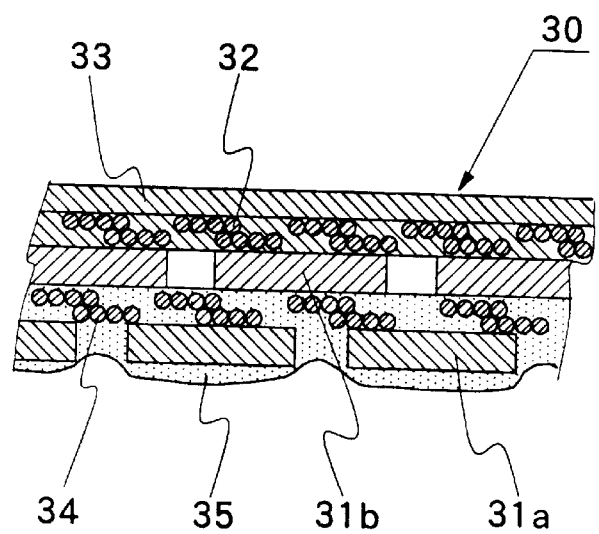
FIG. 9 is a fragmentary sectional view, showing on an enlarged scale major components of the flexible sheathing tube shown in FIG. 8.

Referring now to FIGS. 8 and 9, there is shown a flexible sheathing tube 30, a third embodiment of the invention, the flexible sheathing tube 30 including, from its inner side, inner and outer open helical coil members 31*a* and 31*b*, a protective wire mesh sleeve 32, and an outer skin layer 33. In this case, the inner and outer helical coil members 31*a* and 31 are overlapped one on the other, not directly but through an intermediate or inner wire mesh sleeve 34. An inner coat layer 35 is coated in such a way as to fill in all the interstices between the inner helical coil member 31*a* and the intermediate mesh sleeve 34 which is fitted on the inner coil member 31*a*. In this instance, the mesh sleeve 34 is of metal wire netting similarly to the protective mesh sleeve 32, and likewise has no restrictions in particular with regard to the kind of metal, wire gage, mesh size, netting pattern etc.

In order to fabricate this flexible sheathing tube 30, firstly a metal strip of a predetermined width is wound into the shape of an open helical coil of a predetermined open pitch by the use of a rod-like jig, to form an inner open helical coil member 31*a*. The wire mesh sleeve 34 is then fitted on the helices of the inner coil member 31*a*. Thereafter, a pre-assembly of the inner coil member 31*a* and the wire mesh sleeve 34 is dipped in a solution of a resilient material to form an inner coat layer 35 which covers the pre-assembly all over and fills in all the interstices between the inner coil member 31*a* and the wire mesh sleeve 34, followed by drying treatment to set the inner coat layer 35. After drying, a metal strip of a predetermined width is wound around the wire mesh sleeve 34, similarly into the shape of an open helical coil of a predetermined open pitch to form an outer helical coil member 31*b* around the mesh sleeve 34. Nextly, a protective mesh sleeve 32 and an outer skin layer 33 are successively laminated on the outer helical coil member 31*b* to form the flexible sheathing tube 30.

The sheathing tube 30 of the above-described construction has bending flexibility in all directions. When the sheathing tube 30 is bent, the gap spaces between the respective helices of the inner and outer coil members 31*a* and 31*b* are broadened or narrowed depending upon the degree of bending flexures of the sheathing tube 30. Similarly, the openings in the netting pattern of the wire mesh sleeve 34 are elongated or contracted in relation with bending flexures of the sheathing tube 30. Particularly, the outer helical coil member 31*b* which is wound separately on the outer side of the intermediate mesh sleeve 34 can be bent with a greater degree of freedom. On the other hand, although the inner coil member 31*a* is completely embedded in the resilient material of the inner coat layer 35, it can still be bent in a desired direction because of elasticity of the resilient inner coat layer 35 which fills in even the gap spaces between the individual helices of the inner coil member 31*a*. Accordingly, likewise the sheathing tube 30 as a whole has no particular directionability in its bending flexibility.

Further, in this case, the outer coil member 31*b* is held in abutting engagement not with the inner coil member 31*a* but with the inner coat layer 35, which can produce greater frictional force to suppress axial positional deviations of the outer helical coil member 31*b* to a minimum, preventing the pitch of helices of the outer coil member 31*b* from being disturbed in certain localities by repeated bending flexures, which might cause irregular variations in rigidity in the axial direction of the flexible rod section 2*a*. Of course, the inner helical coil member 31*a*, which is wrapped in the wire mesh sleeve 34 and completely set in the inner coat layer 35 together with the wire mesh sleeve 34, is free from the problem of pitch disturbances of its helices which are retained in predetermined spaced relations by elastic restoring force of the inner coat layer 35.

The flexible sheathing tube 30 has excellent strength in axial direction as well as in radial direction. Although the intermediate wire mesh sleeve 34 is in the form of a tubular netting structure which is elastic by itself, it is sandwiched between the inner and outer coil members 31*a* and 31*b* of rigid metallic material and at the same time embedded in the inner coat layer 35 substantially integrally with the inner helical coil member 31*a*, in a restricted state for movements in stretching and contracting directions, so that it contributes to improve the strength of the sheathing tube 30 in these directions. Accordingly, in various applications, the flexible sheathing tube 30 is free from elongation or contraction as caused by exertion of an axial tensile or compressive force, as well as from collapsing damages as caused by exertion of a large radial compressive force. Because of the freedom from elongation or contraction in the axial direction, the flexible sheathing tube 30 is less likely to suffer from detachment of the outer skin layer 33 which would otherwise be caused by strong stress occurring between the protective mesh sleeve 32 and the outer skin layer 33. Besides, the flexible sheathing tube 30 has sufficient anti-collapsing strength for protection of the internally fitted component parts of the insertion rod.

As gathered from the foregoing description, in addition to the satisfactory flexibility in bending directions, the flexible sheathing tube 30 has excellent properties in strengths against forces acting in axial and radial directions. These properties of the flexible sheathing tube 30 are particularly suitable for the flexible rod section 2*a* of the endoscopic insertion rod 2 or the like. It can be suitably used also for the flexible universal cable 3 or the like which contains elongated fragile component parts.

Especially in case the sheathing tube 30 is used for the flexible rod section 2 of the endoscopic insertion rod 2, it is required to have, along with suitable flexibility in bending directions, a certain degree of rigidity for transmitting a propelling thrust securely as far as the rigid tip end section 2*c* at the distal end of the insertion rod against resistive forces which will act on the rod at the time of intracorporeal insertion. Particularly, an insertion rod for a large intestine endoscope or the like, which is expected to be met by extremely large resistive forces, should have a higher degree of rigidity. Besides, it is desirable for the flexible rod section 2*b* of the insertion rod 2 to have flexibility or rigidity varying in the axial direction thereof. Namely, it is preferred to have higher rigidity at its proximal end, which is connected to the manipulating head assembly 1 of the endoscope, from the standpoint of efficient transmission of thrust or propelling forces as explained above. On the other hand, in order to be able to follow turning movements of the angle section 2*b* of the insertion rod 2 to a certain degree, the flexible rod section 2*a* is preferred to have higher flexibility in its fore end portion which is connected to the angle section 2*b*. More specifically, the flexible rod section 2*a* is preferred to have higher flexibility over a length of some tens centimeters front its fore distal end which is joined with the angle section 2*b*.

Alternatively, in case the flexible sheathing tube is applied to the universal cable 3, it is preferred to have higher rigidity at its opposite connecting ends, i.e., at a fore end to be connected to the manipulating head assembly 1 and a rear or proximal end with a light guide connector to be disconnectibly connected to a light source, thereby preventing breakage of internally fitted components as caused by acute bending force on end portions of the universal cable 3, while retaining higher flexibility in intermediate portions of the cable 3.

As will be understood from the foregoing description, it is an utmost importance to control the bending flexibility of the sheathing tube 30 in the axial direction thereof, depending upon the purpose of use. In this particular embodiment having the inner coil member 31a assembled with the intermediate mesh sleeve 34 and embedded in the inner coat layer 35 to form an integrated inner layer, axially varying characteristics in bending flexibility can be easily imparted to the sheathing tube 30 by way of the just-mentioned integrated inner layer.

More specifically, since the inner coat layer 35 is formed to fill in all the gap spaces between the individual helices of the inner coil member 31a as well as all the openings in the inner wire mesh sleeve 34, integrally embedding the inner coil member 31a and the inner mesh sleeve 34 into the body of the inner coat layer 35, the resistance to bending forces of the sheathing tube 30 can be varied by adjusting the elasticity of the inner coat layer 35. Namely, the characteristics in bending flexibility can be adjusted by changing the properties of the resilient material to be coated on. For example, as a coating resilient material, there may be employed rubber material such as fluorine-contained rubber, silicon rubber or the like, or synthetic resin material such as urethane resin or the like. Of these resilient materials just mentioned, urethane resin has the lowest flexibility. The degree of flexibility can also be adjusted by varying the thickness of coating. The thickness of the inner coat layer 35 can be controlled by way of the kind or mixing ratio of the solvent or by way of the length of dipping time in the solution of the resilient material. It follows that, by the use of these methods, the degree of bending flexibility can be controlled accurately in the axial direction in an extremely facilitated manner.

It is also possible to vary the degree of bending flexibility along the length of the sheathing tube 30 by varying the number of times of dip-coating in the axial direction of the sheathing tube, or alternatively by varying the mesh size of the inner mesh sleeve 34 or by coarsening its netting structure toward the fore end portion of the sheathing tube 30. The bending flexibility can be adjusted more accurately in a predetermined pattern by changing the number of times of dip-coating in the axial direction of a mesh sleeve with different mesh sizes or varying netting structure between fore and rear end portions of the sheathing tube 30.

Of course, the sheathing tube construction just described also contributes to improve the functions of protecting and electrically insulating elongated component parts which are fitted internally of the sheathing tube. Besides, in this embodiment, it is also possible to coat a lubricative material on the surfaces of the inner coat layer 35 to ensure frictionfree sliding contact between the internally fitted component parts and the inner surface of the flexible sheathing tube 30, for the purpose of protecting the internally fitted components in a securer manner. Further, the above-described sheathing tube construction contributes to maintain the interior of the insertion rod in a liquid-tight sealed state, precluding possibilities of internally fitted components being contaminated or deteriorated by contact with a cleaning and/or disinfectant liquid which might otherwise creep into the rod through a bruise or other damaged portion of the outer skin layer 33.

Figure 10:
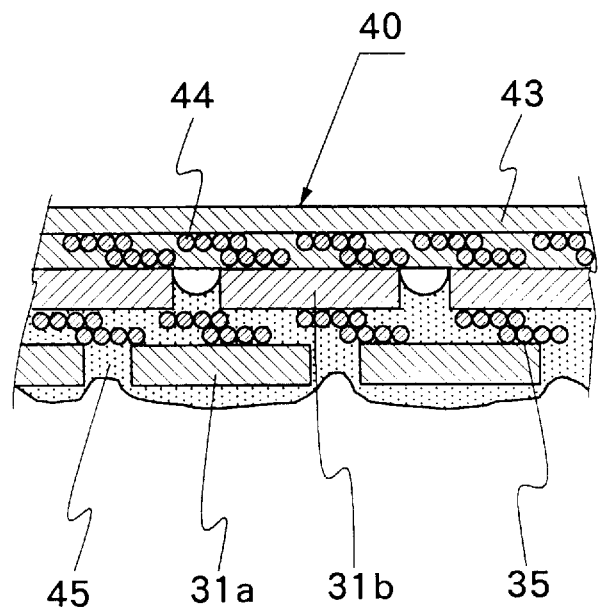
FIG. 10 is a fragmentary sectional view, showing on an enlarged scale major components of a flexible sheathing tube in a fourth embodiment of the invention.

Referring now to FIG. 10, there is shown a flexible sheathing tube 40 as a fourth embodiment of the invention, which includes, similarly to the foregoing third embodiment, inner and outer helical coil members 31a and 31b, a protective mesh sleeve 44, and an outer skin layer 43. An inner mesh sleeve 35, which is fitted between the inner and outer helical coil members 31a and 31b, is integrally embedded in an inner coat layer 45 together with the inner coil member 31a.

In this embodiment, however, the inner coat layer 45 holds not only the inner mesh sleeve 35, which is fitted on the inner helical coil member 31a, but also the outer coil member 31b which is fitted around the inner mesh sleeve 35. Accordingly, the material of the inner coat layer 45 fills in openings in the inner mesh sleeve 35 as well as gap spaces between the individual helices of the inner and outer coil members 31a and 31b. The inner coat layer 45 of this sort can be formed by a method similar to the ones as described hereinbefore in connection with the first and second embodiments.

The flexible sheathing tube 40 of the construction just described is improved in strength in the axial direction because of the inner coat layer 45 which fills up to the gap spaces between the open helices of the outer coil member 31b. Of course, the inner coat layer 45 which is capable of elastic deformations has no possibilities of impairing the flexibility in bending directions. Besides, the inner coat layer 45 fills in the gap spaces between open helices of the inner and outer coil members 31a and 31b through the inner mesh sleeve 35, precluding relative positional deviations which would otherwise occur to the inner and outer coil members 31a and 31b when the flexible sheathing tube 40 is bent. In addition to the resiliency to keep the inner and outer helical coil members 31a and 31b from positional deviations relative to each other, the inner coat layer 45 is preferred to be of a low-friction material such as fluorine-contained rubber or the like for the purpose of ensuring smooth sliding movements of internally fitted component parts without additionally applying a lubricative coating on the inner coat layer.

Figure 11:
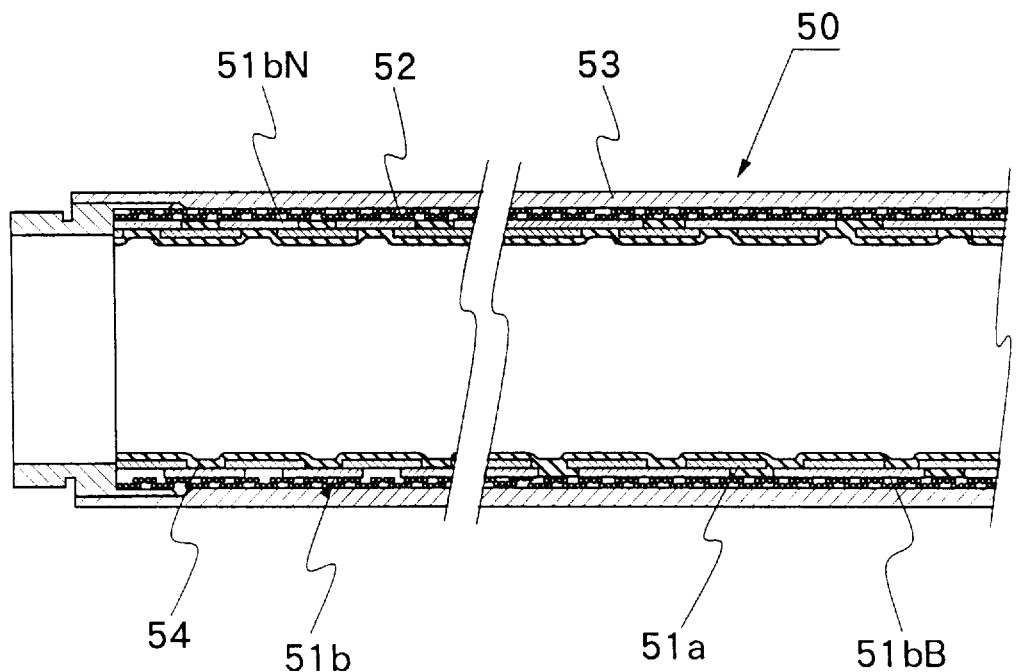
FIG. 11 is a partly cutaway sectional view, showing major component of a flexible sheathing tube in a fifth embodiment of the invention.

Further, in order to impart more distinctive variations in rigidity in the axial direction of the flexible rod section 2a, there may be employed a flexible sheathing tube 50 with a flexible base structure which has inner and outer open helical coil members 51a and 51b as shown in FIG. 11. In this embodiment, of the two coil members, the outer coil member 51b is composed of a couple of helically coiled metal strips of different widths, namely, a broad coil section 51bB occupying almost the entire length of the flexible rod section 2a from its proximal end, and a narrow coil section 51bN occupying a fore end portion of the flexible rod section 2a. Broader and narrower metal strips of the broad coil section 51bB and the narrow coil section 51bN of the outer helical coil member 51b are butt-joined at their meeting ends, and secured to the inner helical coil member 51a by spot welding at a plural number of spots as indicated by the letter W in FIG. 12. Indicated at 52 in FIG. 11 is a protective mesh sleeve, at 53 is an outer skin layer, and at 54 is an inner coat layer.

In this case, since the outer one of the helical coil members 51a and 51b consists of a narrow coil section 51bN in its fore end portion as described above, the sheathing tube 30 enjoys higher flexibility in its fore end portion as compared with the rest of the sheathing tube, which has higher rigidity because of the increased width of the metal strip in the broad coil section 51bB on the side of the proximal end of the sheathing tube. The greater the difference in width of the coiled metal strip between the narrow coil section 51*b*N and the broad coil section 51*b*B, the greater becomes the difference in flexibility. Accordingly, when applied to the insertion rod 2, the flexible sheathing tube 50 of this construction can ensure sufficient rigidity in its proximal end portion on the side of the manipulating head assembly 1 for transmitting a propelling thrust toward the fore end of the rod upon introduction into an intracavitary portion of patient, along with sufficient bending flexibility in its fore end portion for following flexing movements of the angle section 2*b* of the rod.

Figure 12:
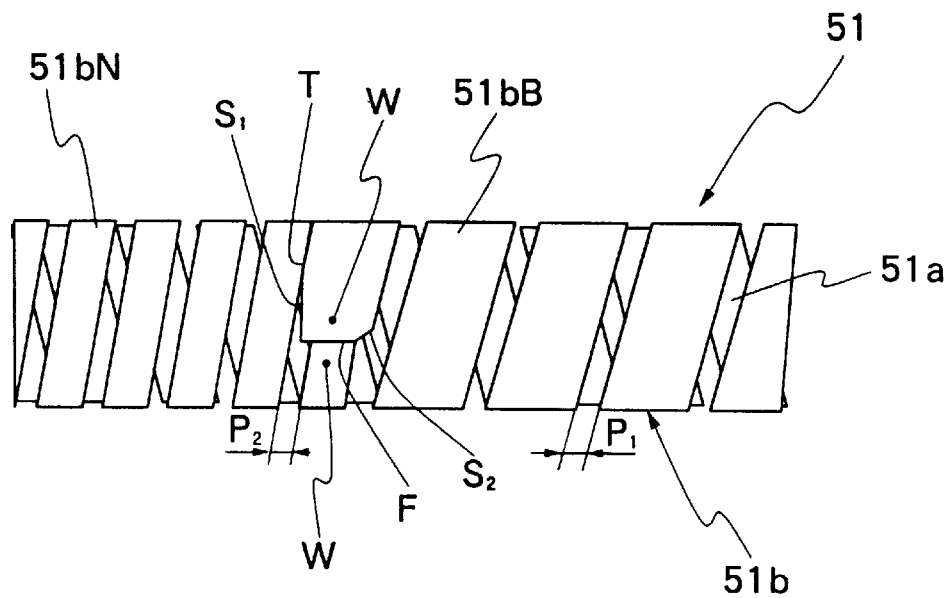
FIG. 12 is a schematic view of an outer helical coil member, showing a joint portion of broad and narrow helical coil strips.

In this regard, as shown in FIG. 12, because of the difference in width of the joining ends of the broad and narrow coil sections 51*b*B and 51*b*N of the outer coil member 51*b*, the meeting end of the broad coil section 51*b*B is narrowed down or tapered off by oblique side cuts S1 and S2 into a width which is substantially same as or slightly broader than the width of the meeting end of the narrow coil section 51*b*N. In this instance, the joining end of the broad coil section 51*b*B should preferably be narrowed down to a greater degree by the oblique side cut S1 on the side of the narrow coil section 51*b*N than by the side cut S2 on the opposite side. By doing so, the front end face F of the broad coil section 51*b*B is located in a slightly offset position to the right in the drawing relative to the center line intermediate of the width of its coil strip. This is because the helices of the broad coil section 51*b*B are spaced from each other by a gap space P1 which is broader than a gap space P2 between the helices of the narrow coil section 51*b*N, and the helices in the narrow coil section 51*b*N are disposed at a larger angle with the axis of the flexible coil structure 51. Namely, in this instance, arrangements are made such that an adjacently located helix of the narrow coil section 51*b*N first approaches and comes into abutment against the broad coil section 51*b*B at a point T which coincides with the upper end of the larger side cut S1.

In the case of the flexible coil structure of the above construction, a gap space slightly broader than the gap space P1 between the helices of the broad coil section 51*b*B is formed on the right side of the spliced ends of the broad and narrow coil strips, in an imbalanced relation with the width of a gap space on the other side of the spliced ends. However, since the fore end face F of the joining end of the broad coil section 51*b*B is joined with the narrow coil strip at a slightly offset position toward the side away from the narrow coil section 51*b*N, which is in turn located as close to the tapered joining end of the broad coil section 51*b*B as possible, the flexible coil structure 51 as a whole exhibits a smooth change in flexibility or rigidity across the spliced ends, thus precluding an abrupt change which would be normally experienced with spliced ends involving a gap space greater than P1 on one side thereof. In this instance, the width P1 of the gap spaces between the helices of the broad coil section 51*b*B are set at a suitable value which is small enough for preventing the protective mesh sleeve 52 from sinking down between the respective helices into a corrugated form under pressure of a synthetic resin material in an extrusion-molding stage for the outer skin layer 53. Accordingly, the outer skin layer 53 can be formed in a uniform thickness on the protective mesh sleeve 52.

Figure 13:
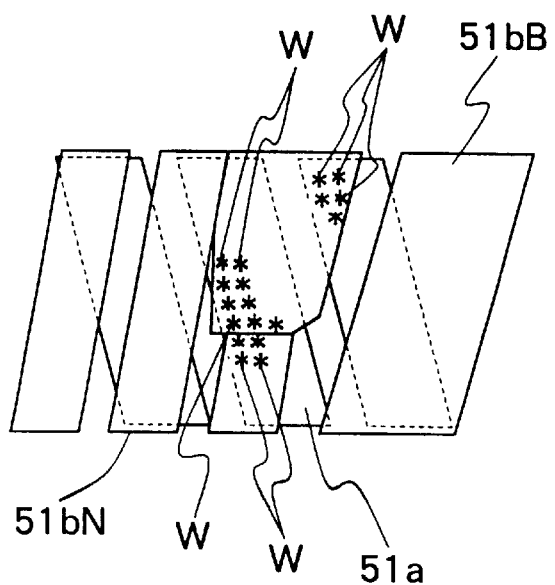
FIG. 13 is a schematic illustration of another joint arrangement for broad and narrow helical coil strips.

The broad coil section 51*b*B which is tapered into a smaller width toward the end face F by the above-described oblique side cuts is less likely to recoil at the spliced end. In this regard, as shown particularly in FIG. 13, recoiling at the joined end can be prevented by spot-welding the joining end portion to the inner helical coil member 51*a* at a plural number of spots along the oblique side cuts S1 and S2 as indicated by letters W. Further, wasteful spaces can be minimized by rounding off the edges of the oblique side cuts S1 and S2 by the use of a file or the like.

In consideration of a relatively large difference in bending flexibility between the narrow coil section 51*b*N and the broad coil section 51*b*B, it may be conceivable that, when the flexible sheathing tube 30 is bent abruptly at the spliced portion of the outer coil member 51*b*, the narrow coil section 51*b*N could be caused to slide along with the inner coil member 51*a* and to ride over the broad coil section 51*b*B. However, on such an occasion, the narrow coil section 51*b*N which is substantially held in abutting engagement with the broad coil section 51*b*B at the point T is caused to rock on the point T at the upper end of the angular side cut S1 to increase the area of abutting engagement with the adjacent helix of the broad coil section 51*b*B. Accordingly, axial movements of the narrow coil section 51*b*N at the abutting point are suitably suppressed to a restricted range, preventing same from riding over the broad coil section 51*b*B and exerting such an excessively large force on the protective mesh sleeve as would cause defoliation of the outer skin layer 53.

What is claimed is:

1. A flexible tube construction for an endoscopic insertion tube encasing at least one elongated flexible component of an endoscopic examination instrument within a hollow internal passage of the tube, comprising:

a multi-layered wall including at least, from the side of the internal passage, an open helical coil structure formed of a flat metal strip having a predetermined width wound in a cylindrical shape in a predetermined open pitch so as to provide required flexibility in bending directions together with compressive strength, a protective mesh sleeve fitted on said helical coil structure, and an insulating outer coating layer formed on said protective mesh sleeve; and an inner coat layer of a resilient material formed on the inner periphery of said open helical coil structure to cover inner surfaces of helices of said metal strip completely, filling in gap spaces between open helices of said helical coil structure and keeping the at least one elongated flexible component in the internal passage out of contact with helices of said metal strip of said helical coil structure.

2. A flexible sheathing tube as defined in claim 1, wherein said inner coat layer is formed of an electrically insulating rubber material.

3. A flexible sheathing tube as defined in claim 1, wherein said flexible base structure comprises a double coil structure with inner and outer open helical coil members having open helices wound in opposite directions with a predetermined open pitch and fitted one on the other in an overlapped state.

4. A flexible sheathing tube as defined in claim 3, wherein said inner coat layer also fills in gap spaces between open helices of said outer coil member.

5. A flexible sheathing tube as defined in claim 1 or 3, wherein said inner coat layer has means to vary bending flexibility in the axial direction of said flexible sheathing tube.

6. A flexible sheathing tube as defined in claim 5, wherein said inner coat layer has means to provide higher bending flexibility at one end of said flexible sheathing tube than at the other end thereof.

7. A flexible sheathing tube as defined in claim 3, wherein a second mesh sleeve is fitted between said inner and outer coil members of said double coil structure.

8. A flexible sheathing tube as defined in claim 7, wherein said inner coat layer is positioned on the inner periphery of said double coil structure in such a manner as to embed said inner coil member and said second mesh sleeve therein.

9. A flexible sheathing tube as defined in claim 7, wherein said inner coat layer is positioned on the inner periphery of said double coil structure in such a manner as to embed said inner coil member and said second mesh sleeve therein and filling in gap spaces between open helices of said outer coil member.

10. A flexible sheathing tube as defined in claim 7, wherein said second mesh sleeve is formed in a netting pattern with a lower net density toward one axial end of said flexible sheathing tube.

11. A flexible sheathing tube as defined in claim 3, wherein one of said inner and outer coil members is composed of broad and narrow coil sections formed of metal strips of different widths and joined together end to end at a predetermined point in the axial direction thereof to vary flexibility of said sheathing tube, said broad coil section having a broad metal strip gradually narrowed down from opposite sides at a joining end portion to be connected to said narrow coil section.

12. A flexible sheathing tube as defined in claim 11, wherein said joining end portion of said broad coil section is narrowed down to a greater degree on the side of said narrow coil section from a predetermined initial narrowing point.

13. A flexible sheathing tube as defined in claim 12, wherein a terminal helix at the joining end of said narrow coil section is held in abutting engagement with said initial narrowing point.

* * * * *